United States Patent [19]

Pratt, Jr. et al.

[11] Patent Number: 4,913,157

[45] Date of Patent: Apr. 3, 1990

[54] ULTRASOUND METHOD AND APPARATUS FOR EVALUATING, IN VIVO, BONE CONDITIONS

[75] Inventors: George W. Pratt, Jr., Wayland, Mass.; Paul Duchnowski, Staten Island, N.Y.

[73] Assignee: Analog Devices, Inc., Norwood, Mass.

[21] Appl. No.: 870,175

[22] Filed: Jun. 3, 1986

[51] Int. Cl.⁴ ............................................. A61B 8/00
[52] U.S. Cl. ................................. 128/661.03; 73/597
[58] Field of Search .......................... 73/597, 599, 602; 128/660-663

[56] References Cited

U.S. PATENT DOCUMENTS 3,477,422 11/1969 Jurist et al.
3,847,141 11/1974 Hoop ............................... 73/632 X
4,361,154 11/1982 Pratt, Jr.
4,421,119 12/1983 Pratt
4,774,959 10/1988 Palmer et al. ................... 128/660.06

OTHER PUBLICATIONS

Langton, C. M. et al., "The Measurement of Broadband UTS Attenuation in Bone", MEP Ltd. 1984 (Energy in Medicine) pp. 89-91.
Bhagat, P. K., et al., "Microprocessor-Based System for UTS Tissue Characterization", Med. Instrumentation, vol. 14, #4 (Jul.-Aug. 1980), pp. 220-223.
Y. W. Lee: The Statistical Theory of Communication, Wiley 1960.
Ashman et al.: "A Continuous Wave Technique for the Measurement of Elastic Properties of Cortical Bone", *Journal of Biomechanics*, vol. 17, pp. 349-361, 1984.
"The Investigation of Bone's Substructure Using Megahertz Sound and a Porous Model", Bruce Martin et al., *The American Society of Mechanical Engineers*, pp. 1-11.
"Ultrasonic Technique for the Evaluation of Bone Fractures", George T. Anast, M.D. et al., *U.S. Diagnosis in Fractures*, pp. 157-159.
"Physical Principles of Ultrasonic Diagnosis", P. N. T. Wells, vol. I, 1969, *Academic Press*, London-New York, pp. 1-23.

(List continued on next page.)

*Primary Examiner*—Francis Jaworski
*Attorney, Agent, or Firm*—Wolf, Greenfield & Sacks

[57] ABSTRACT

A system for analyzing bone conditions, particularly (but not solely) for diagnosing osteoporosis and periodontal bone disease in humans. An ultrasonic signal (generally a pulse) having at least two components of distinguishable waveshape or frequency content in a range from about 100 kHz to about 3 MHz is launched transdermally into the patient, through a bony member such as the patella, and received at the other side. The transmission through the bony member and surrounding soft tissue varies in both amplitude and phase as a function of frequency, and the velocity of transmission varies between the bony member and the soft tissue. A variety of techniques are employed for analyzing the transmission of the ultrasonic signal to assess bone condition. These include at least: comparing the transit times through the bony member of energy in a first frequency range and energy in a second frequency; evaluating the transfer function through the bony member (i.e., gain and/or phase) of the portion of the signal travelling through the bony member; evaluating a gain function of the power spectrum of the portion of the signal transmitted through the bone, including the evaluation of the area under such gain function and/or the magnitude and location of its peak amplitude. The velocity of ultrasound energy through the bony member also may be deduced by determining the duration of travel of the ultrasound signal through the bony member and soft tissue and adjusting such composite velocity by a soft tissue normalization factor. Such information is then compared to a data base of prior measurements for the same patient and/or for the population at large, to determine a probability that the patient's bone condition is abnormal.

88 Claims, 8 Drawing Sheets

OTHER PUBLICATIONS

"Strength of Biological Materials", Hiroshi Yamada, M.D., *The Williams & Wilkins Company Baltimore*, 1970, pp. 53–57.

"Ultrasonic Assessment of Early Callus Formation", by Stanley A. Brown SB, DEng et al., *Biomedical Engineering*, vol. 11, No. 4, Apr. 1976.

"Ultrasonic Prediction of Delayed or Nonunion of Fractures", by Stanley A. Brown et al., *Proceedings of the Fifth New England BioEngineering Conference*, Pergamon Press, pp. 229–233.

"Comparison of Two Formulae for in Vivo Prediction of Strength of the Femur", by B. Sherwood Mather, *Aerospace Medicine*, Dec. 1967, vol. 38, No. 12, pp. 1270–1272.

"Ultrasonics and Selected Physical Properties of Bone", by Walter Abendschein, M.D. et al., *Clinical Orthopaedics and Related Research*, No. 69, Mar.–Apr., 1970, pp. 294–301.

"Noninvasive Bone Mineral Assessment: Another Opportunity for Diagnostic Imaging Services", *J. Health Care Technol.*, vol. 2, No. 3, at pp. 183, Winter 1985.

Greenfield et al.: "Measurement of the Velocity of Ultrasound in Human Cortical Bone In Vivo", *Radiation Physics*, Mar. 1981.

Martynov et al., "Arrangement for Determining the Elastic Properties in Samples of Mineral Raw Materials and other Materials", *Bulletin of Inventions*, Nov. 21, 1959 (translated from Russian).

Cohn: "Techniques for Determining the Efficacy of Treatment of Osteoporosis", *Calcified Tissue International*, vol. 34, No. 5, 1982.

Wilson and Madsen, "Dichromatic Absorptiometry of Vertebral Bone Mineral Content", *Investigative Radiology*, Mar.–Apr., 1977, vol. 12.

D. I. Rosenthal: "Radiographic Evaluation of Osteopenia".

Cann: "Low-Dose CT Scanning for Quantitative Spinal Mineral Analysis", *Radiation Physics* at pp. 813–815, Sep. 1981.

McDavid et al.: "Estimation of Chemical Composition and Density from Computed Tomography Carried Out at a Number of Energies", *Investigative Radiology*, Mar.–Apr. 1977, vol. 12.

Dunn et al.: "Measurement of Bone Mineral Content in Human Vertebrae and Hip by Dual Photon Absorptiometry", *Work in Progress*, Aug. '80.

Cheney et al., "Cannon-Bone Fracture in the Thoroughbred Racehorse", *Medical and Biological Engineering*, Sep. 1973.

Shryver: "Bending Properties of Cortical Bone of the Horse", *Am. J. Vet. Res.*, vol. 39, No. 1, Jan. 1978.

Chamay and Tschantz: "Mechanical Influences in Bone Remodeling Experimental Research on Wolff's Law", *Journal of Biomechanics*, vol. 5, pp. 173–189.

Gennant et al.: "Quantitative Computed Tomography of Vertebral Spongios A Sensitive Method of Detecting Early Bone Loss After Ophorectomy", *Radiology*, at pp. 342–343, Jul. 1983.

M. Madsen: "Vertebral and Peripheral Bone Mineral Content by Photon Absorptiometry", *Investigative Radiology*, Mar.–Apr. 1977, vol. 12.

K. H. Okumura: "Preventive Diagnosis of Breakdown", MIT 1978.

|  | AVERAGE RATIO | STD. DEV. | T | t (98%) |
|---|---|---|---|---|
| RUNNER | 1.450 | .0884 | | |
| NORMALS | 1.366 | .1031 | 1.552 | 2.423 |
| OSTEO | 1.265 | .1152 | 2.4759 | 2.423 |

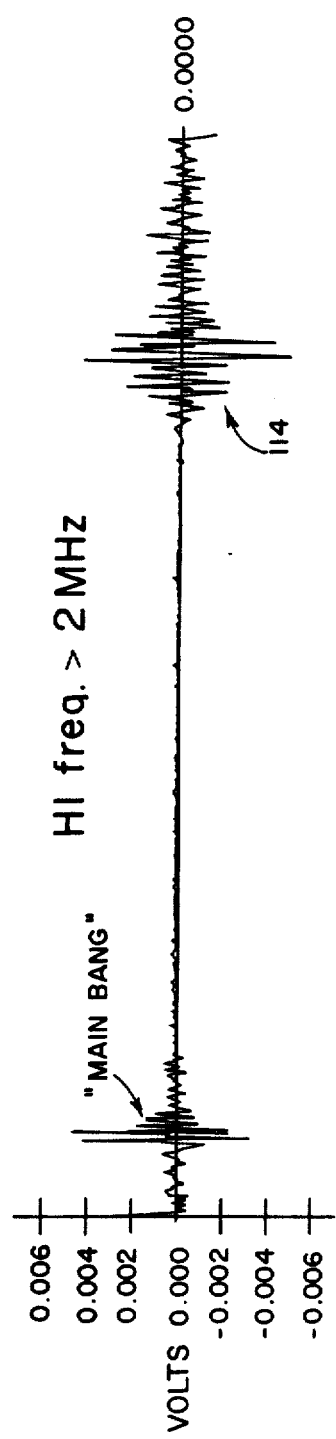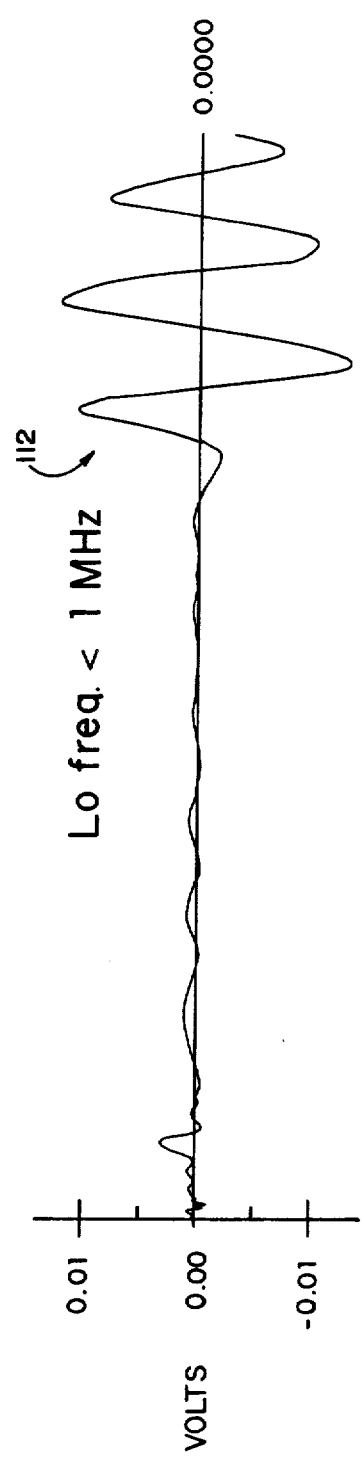
FIG. 10B
FIG. 10A

ULTRASOUND METHOD AND APPARATUS FOR EVALUATING, IN VIVO, BONE CONDITIONS

BACKGROUND OF THE INVENTION

1. Field of the Invention

This invention deals generally with diagnostic methods for determining the condition of bones. In particular, it discloses a method for non-invasively, in vivo, determining the condition of certain bones in humans and animals. This information can be used to evaluate whether or not the subject has any disorders relating to variations in bone condition, such as osteoporosis (abnormally low bone density) or osteopetrosis (abnormally high bone density).

2. Discussion of the Problem and Objects of the Invention

This invention pertains to detecting bone disease and other abnormal bone conditions. The invention is intended specifically for evaluation and diagnosis of humans, but with obvious modification of the illustrative embodiments, the invention could be used to evaluate animal bones, also. The main object is to diagnose the presence of osteoporosis. However, other conditions may also be detected using this method, including bone condition variations following renal failure and periodontal disease due to bone deterioration The invention may also be useful both for detecting fractures and for assessing, quantitatively, the healing of fractures.

The human skeleton is composed of tubular (long and hard) and cancellous (spongy) bones, each of which is composed of, specific proportions of cortex (compact bone) and trabeculae (connective strands). Tubular bones, which are composed largely of cortex, dominate the appendicular skeleton that makes up the limbs; cancellous bones, which are composed primarily of trabecular bone, dominate the axial skeleton of the vertebral column and pelvis.

In both cortical and trabecular bone, the collagen fibrils extend throughout. The difference between the two is actually one of degree, depending upon the form the network of collagen fibrils takes. In general, the fibrils may be separated such that the network is a network of rods. They may also be more closely spread, so that the network appears as a network of plates connected by rods. In both cases, a certain volume of the bone will comprise mineralized collagen fibrils, and a certain volume will comprise fluid known as "marrow."

Whether or not a particular bone assumes a trabecular or cortical formation is thought to depend largely upon the function that bone serves. The method of bone formation is not well understood; however, it is believed that the process of bone accretion responds in some manner to stresses experienced by the bone. Therefore, that region of a bone that experiences relatively high stresses, such as the diaphysis of the tibia of the leg, tends more toward cortical bone Regions of a bone that experience low stress tend more to be trabecular. In most sites of trabecular bone, the trabecular mass is surrounded by a relatively thin layer of cortical bone The patella (kneecap) is mostly trabecular with a subcortical layer just beneath the anterior surface.

The principal target of the invention, osteoporosis, is a disease of unknown cause which afflicts people, generally, as they age. Osteoporosis afflicts women more often than men, and of women, more often after menopause. White women are more often stricken than women of other races Osteoporosis is manifest as an absolute decrease in bone tissue mass. The bone that remains is, however, normal A person suffering from osteoporosis loses a greater proportional amount of trabecular bone than cortical bone Common manifestations of osteoporosis are a hunched back, caused by crush fractures of the vertebrae, and fractures of the neck, the femur (upper thigh bone) and distal end of the radius (wrist bone).

Osteoporosis is a particularly insidious condition, because during its early phases physical deformity is not evident. Because osteoporosis develops progressively, early diagnosis and appropriate treatment may turn an otherwise serious onslaught Additionally, because of the mode by which bone is formed, an enhanced exercise regimen during the patient's younger years, coupled with an appropriate diet, has been thought to also minimize the effects of the condition. With women, it is appropriate to begin these programs prior to menopause. The diagnosis and treatment of osteoporosis is complicated by the fact that every patient has a different "normal" bone density; thus it is beneficial to generate a historical record of the changes in some property of the individual patient's bones (i.e., density or elasticity) and to make a diagnosis, at least in part, on the basis of historical trends.

Another target of the invention, periodontal disease, involves loss of bone in the mandible and maxilla, with consequential loosening of teeth. Heretofore, the progress of bone loss in the jaw has been monitored with X-rays, which can only reveal the presence of periodontal disease after substantial bone loss has already occurred.

Consequently, it is highly desirable to provide a means for detecting changes of bone condition (including, but not limited to the loss of bone material and attendant decrease in bone density and elasticity). Optimally, such means is non-invasive, accurate, sensitive, easy to use and can be made generally available. This is not, however, true of the prior art techniques, in general.

Recently, several methods have been proposed for the early diagnosis of osteoporosis. These methods include Neutron Activation Analysis of Total Body Calcium (TBC), single photon absorptiometry (of the wrist and oscalcus) and dual photon absorptiometry (of the spine and neck of the femur), Computer Aided Tomography (CAT scanning) and methods of ultrasound analysis.

The TBC method, briefly described, is as follows: TBC requires a source of fast neutrons, having energy of approximately 14 MeV. A beam of neutrons is directed at the subject. Depending upon the energy of the incident neutron beam, the nuclei of certain atoms capture the neutrons and become excited. The excited isotopes revert to a stable condition by emitting one or more gamma rays, either immediately (on the order of 10–12 seconds) or after a decay period characteristic of the activation product. The energy of the emitted gamma ray characterizes the target element. Calcium emits gamma rays at an energy of 3.1 MeV. The intensity of the gamma rays, i.e., a count rate per unit volume, indicates the amount of the subject element present. A disadvantage of TBC is that it convenienty measures only the total body calcium, thus, localized change in bone mass, as may be present in early stages of osteoporosis, will not be discernible. Further, TBC facilities require a neutron source, such as a nuclear reactor, a cyclotron or a radioactive material. They also include a large and sophisticated machine, and thus are relatively expensive, and rare. Thus, they are not available for most patients. As can be expected, this method is relatively expensive. Finally, a large radioactive dose of 0.3–0.5 rem is required, inhibiting repeat testing.

Photon absorptiometry is a technique that depends upon the absorption by a material, of discreet energy photons. In single photon absorptiometry, a single energy source emits a beam of monochromatic photons. The intensity of transmitted photons attenuates exponentially with respect to the mass of the substance in the path of the photons. Knowing the distance travelled, the density of the intervening substance can be determined. The problem with single energy photon devices is that they cannot resolve the effect of multiple attenuating layers, such as soft tissue surrounding bone.

Thus, dual photon absorptiometry is used According to this method, a single source having photons of two discreet energies, such as $^{153}$Gd, or two discreet energy sources such as $^{125}$I and $^{241}$Am are used. Two equations, each in two unknowns, result, relating the unattenuated and the attenuated photon intensities to the densities of the two substances. The two equations can be solved, and the two densities can be determined As is the case with respect to TBC, the equipment is relatively expensive and rare. Further, because soft tissue is made up of different components of skin, fat and muscle, a "fat/-lean" adjustment factor must be used.

Density of bones can also be determined by using a CAT scan. A CAT scanner is a device which computes an image from multiple incidents of X-ray transmission. The patient is placed in a hollow cyclinder having X-ray sensitive receivers around the entire circumference. An X-ray source revolves around the patient, sending individual beams of X-rays through the patient to be received by the receiver at the opposite end of a diameter of the cylinder. This transmission is repeated for the entire circumference of the cylinder. The intensity of X-rays received by the receiving sensor is related to the total density of the path through the patient's body. A large number of these readings are taken as the transmitter circumnavigates the patient Sophisticated computerized analysis collates the readings received at each receiver, and generates a map of the density of a thin slice of the patient's body taken parallel to the plane defined by the many transmitted beams.

The output of the CAT scan is a density map. A CAT scan through bony areas will provide information relative to the density of the bones. The asserted advantages of the CAT scan are that it is a reproducible and reliable device, that it has been well tested in other related fields. Further, it quantifies the trabecular and cortical density separately. Thus, the exact density of the cancellous bone may be determined, without any averaging effect caused by the presence of the surrounding compact cortical bone.

Drawbacks to the CAT scanning technique are that the equipment is expensive and that it is not available in many communities. Further, it is not portable and may be regarded as traumatic for certain patients. Administration of CAT scans must be done by licensed doctors of radiology or technicians associated with radiologists, thereby further increasing the cost. Finally, CAT scans involve X-ray exposure to the patient, which is seen as undesirable by some doctors and patients. "Patient", as used herein, refers to both human and animal subjects.

For in vivo, non-invasive analysis of bones in humans and other animals, measurement by use of ultrasound also has been performed. Such measurement is complicated, though, by the presence of soft tissue surrounding most bones. The speed of an ultrasound signal injected transdermally is affected by passage through the soft tissue surrounding the bones, as well as by passage through the bone(s) of interest It is possible to minimize the effect of the soft tissue; however, prior attempts to do so have been encumbered by requirements for rather sophisticated echo analysis and careful measurement. See, for example, U.S. Pat. No. 4,361,154, "Method for Establishing, In Vivo, Bone Strength."

Thus, the several objects of this invention are: (1) to evaluate bone condition in patients with a non-invasive, in vivo technique; (2) to evaluate bone condition without subjecting patients to substantial doses of X-rays; (3) to evaluate bone condition in patients economically and quickly; (4) to provide a method or methods of evaluating bone condition that may be performed safely and economically many times over the course of several years; and (5) to provide a method or methods of evaluating bone condition that may be performed by a technician without the need for expensive equipment, especially careful measurement or complex analysis.

As used herein, "patella" refers to the thick, flat triangular bone that forms the anterior part of the knee; "kneecap" refers to the patella and surrounding soft tissue; "tibia" refers to the anterior bone of the lower leg; "shin" refers to the tibia and surrounding soft tissue.

BRIEF SUMMARY OF THE INVENTION

According to the present invention, bone condition is determined by sending an ultrasound signal through a portion of bone, and analyzing the signal that is received. The ultrasound signal preferably contains at least two components of distinguishable waveshape or frequency content. These components may be in either pulse or continuous-wave format, or some combination thereof. Hereinafter, except as expressly appears otherwise, where the term "pulse" is employed, it is intended to include both finite duration and continuous-wave signals. If narrow band signals are used, they may be transmitted at the same time (e.g., as part of a composite waveform) or at different times Alternatively, a broadband signal may be employed. This may, for example, be a signal containing energy over a large frequency range, such as from about 100 kHz to about 3 MHz. The differences in the propagation of the two (or more) components contains information on the condition of the bone.

The invention is believed to operate on the principle that the speed of transmission of an ultrasound signal through a medium is related to the density and elasticity of the medium. It further relies on the observation that the attenuation is frequency-dependent. Due to the varied nature of bone, ranging from cortical bone to trabecular bone, it is not possible to exactly state the relationship between the velocity of any ultrasound signal and the density and/or elasticity of the medium. However, models have been proposed for both cortical and trabecular bone that correlate well with results from experiments performed on bone that is mostly cortical and mostly trabecular, respectively. Thus, the relative speed of ultrasound signal propagation may be used as an indicator of susceptibility of bone to breakage A pair of transducers is used, for sending and receiving the pulse. These transducers are connected to an ultrasound pulse generator and to a signal receiving and processing system, respectively. The transducers are positioned at two different locations adjacent the bone such that the ultrasound signal is launched into and through the bone and soft tissue, and intercepted by the receiving transducer.

The bone to be measured preferably is surrounded by only minimal soft tissue and its surface preferably has opposing portions, such that sound energy may be coupled into and out of these portions by faces of sending and receiving transducers arranged substantially in parallel. The sound path of the first arriving portion of the ultrasound signal thus begins at the face of the sending transducer, travels though the soft tissue covering the bone, through the bone to and through the soft tissue separating the bone from the receiving transducer, and finally to the receiving transducer. (Portions of the ultrasound signal may propagate over other, acoustically longer paths and will therefore arrive later).

Various bone sites may be used for test purposes, but the kneecap has been found to be a favorable location due, in part, to the fact that (a) the distance through the soft tissue layers surrounding the patella is much less than the distance through the bone and (b) there exists an acoustic propagation path through the soft tissue overlaying the patella which is approximately parallel to, and nearly the same distance as, the propagation path through the patella and soft tissue layers. Other useful sites are, for example, the tibia, the maxilla and the mandible. Examination at the two latter bones may, it is hoped, provide a way to detect periodontal disease.

In a first embodiment of the invention, the received signal is processed to filter out noise, thereby permitting more precise determination of the duration of ultrasound propagation delay. The distance between the sending face and the receiving face of the transducers is measured automatically by digital caliper, and the velocity through the bone is calculated. In calculating such velocity, it is preferable to first correct the measured propagation delay for error introduced by the finite thickness of the soft tissue cover surrounding the bone.

The velocity measured through the bone and soft tissue, or the velocity corrected for soft tissue, may be compared to various data compilations. First, over time, a history of the patient under examination may be created, so that changes in velocity, indicating changes in bone density and/or elasticity, can be noted. This type of comparison charts the development of the disease or the rehabilitation of the patient. Additionally, a data base comprised of bone density, elasticity and/or velocity may be compiled for a wide cross-section of the population, including in that cross-section both healthy and diseased individuals of all relevant ages. A patient's bone density, elasticity and/or velocity measurements may be compared with the information in this data base automatically, based on selected threshold criteria, to predict within clinically useful confidence levels whether the patient's bone is healthy or not, or to assess the probability that the patient is suffering from a bone disease.

In a second embodiment of the invention, measurement of the distance between the sending and receiving transducer faces is not required. The ultrasound signal emitted by the sending transducer has at least two separate frequency components in the range from about 100 kHz to about 3 MHz. after propagating through the patient's soft tissue and bone, a low frequency component of this signal arrives at the receiving transducer first, followed by a later arriving high frequency component. It has been found that the ratio of the arrival times of the two components is a good predictor of bone condition. Other measurements also appear to be good predictors, such as the ratio (as a function of frequency) of the power spectra of the received low frequency (i.e., below 1 MHz) components to the applied excitation in the same range. This ratio is referred to as a "gain function." The peak amplitude and the area under such a gain function can also be used as a predictor.

Moreover, these different predictors can be used in tandem, to achieve a predictor of even greater reliability.

The foregoing, and other as yet unstated, objects, advantages and features of the invention will become more apparent from the following detailed description and the claims appended thereto, all of which should be read in conjunction with the accompanying drawing.

BRIEF DESCRIPTION OF THE DRAWING

In the drawing,

FIGS. 10A and 10B are schematic illustrations of a time-domain high frequency waveform and a time-domain low frequency waveform produced by the method of FIG. 9.

DETAILED DESCRIPTION OF THE EMBODIMENTS

Figure 1:
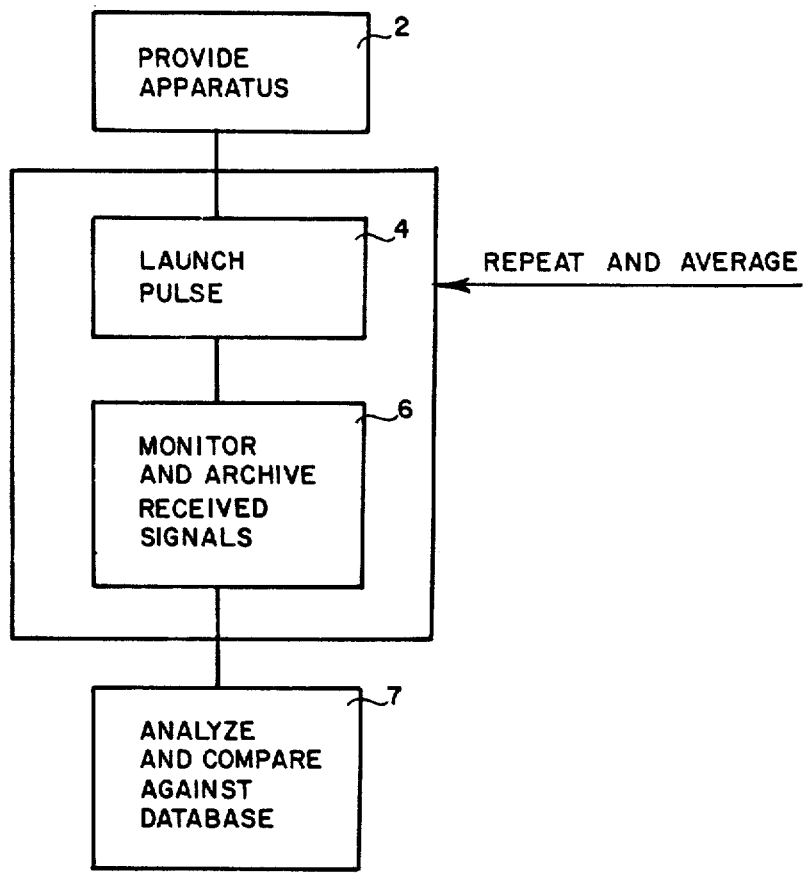
FIG. 1 is a flow chart outlining in general the steps of the method of the present invention.

Turning to FIG. 1, a schematic flow chart illustrates the basic steps of the method. The first step, of course, labeled with the numeral 2, entails providing an appropriate apparatus to conduct the generation, administration and measurement of ultrasonic signals. The apparatus, which will be discussed more fully below in connection with FIG. 4, consists generally of an ultrasonic signal (e g., pulse) generator, a pair of transducers and a signal detection and analysis unit.

Figure 2:
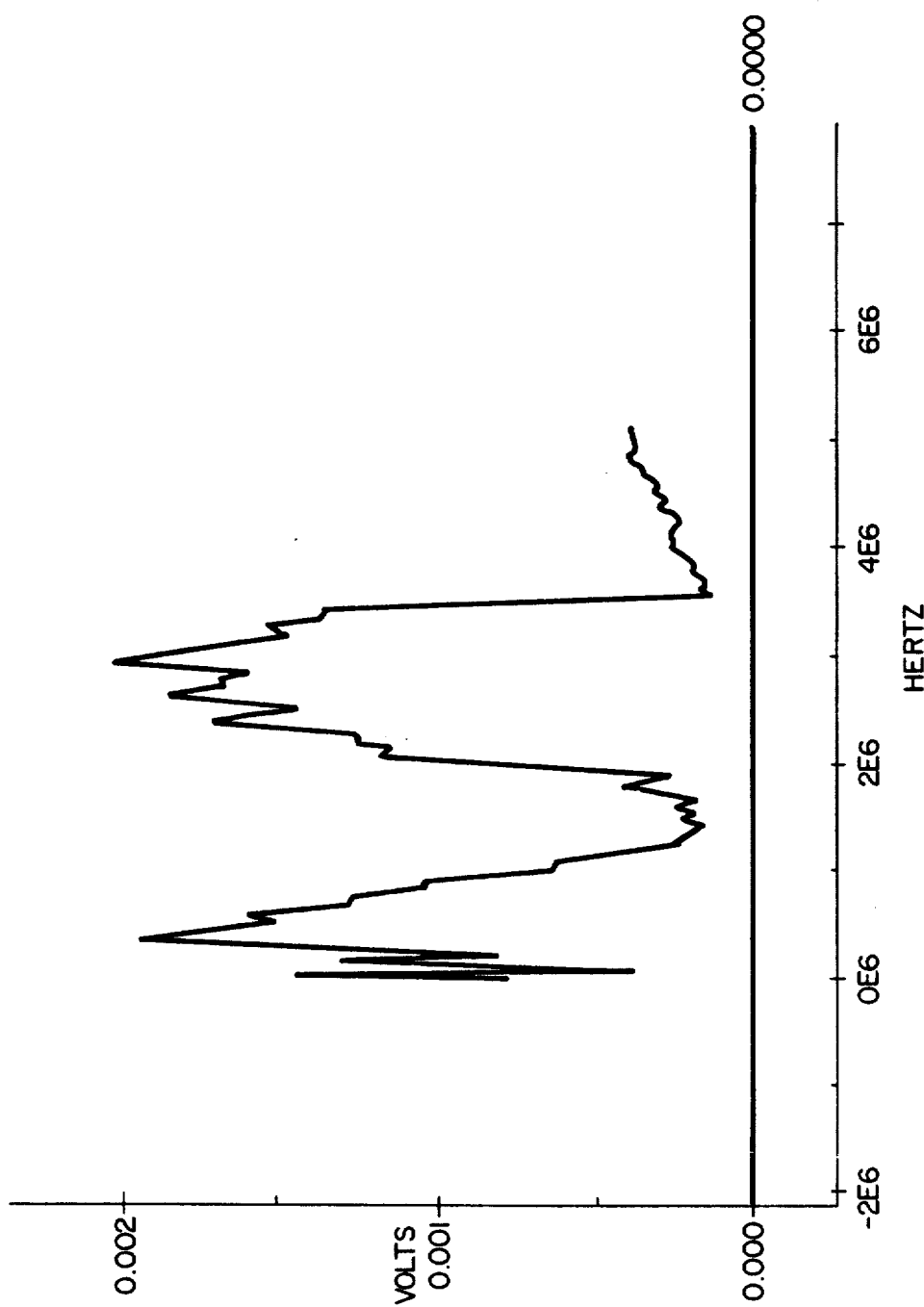
FIG. 2 is an illustration of the spectrum of the ultrasound signal emitted from a transducer useful in the apparatus of FIG. 4.

As indicated in block 4, a broad band waveform generator is provided to launch from one of the transducers a pulse of sound containing energy components from about 100 kHz to about 3 MHz, for a duration of approximately $2\times10^{-6}$ seconds. The spectrum of the excitation from an exemplary apparatus (discussed below) is shown in FIG. 2; note that the signal amplitude and power may vary widely over that spectrum. (For this reason, as stated above, separate narrow band signals at about 250 kHz and 2.5 MHz could alternatively be used.) The launching of the pulse is recorded by a data acquisition system, which stores it on a magnetic disk or other archivable medium. It may also be displayed on a cathode ray tube or other suitable display device. The next step, 6, includes monitoring acoustic excitations at the receiving transducer. These excitations include background noise, the first arriving signal transmitted through the bone and soft tissue, and subsequent arriving signals transmitted through the bone and soft tissue. Step 6 also includes generating electronic signals corresponding to the acoustic excitation, storing the record of receipt of those excitation signals by means of the data acquisition system, and displaying the record of receipt of the signals on the same cathode ray tube display. In step 7, the received signals obtained from steps 4 and 6 are processed (by a variety of techniques, which may include analog or digital filtering and a variety of computations) to produce one or more derived measurements. These derived measurements are then compared with a data base of information correlating received signal characteristics against patient-categorizing factors such as (but not limited to) age, sex, race and the patient's bone condition.

It is good practice, although not essential, to reduce error due to random noise by repeating steps 4 and 6 several times and averaging the results.

The patient's soft tissue and bone act, in part, like a complex network with transmission properties varying as a function of frequency. The resulting alteration of the ultrasound input excitation as it passes through the patient provides, at the receiving transducer, a very much altered spectrum. This spectrum contains at least two separate pulses, or signals, which arrive at different times. An evaluation of the characteristics of these pulses by either analog or digital processing means, both compared with each other and against the original, transmitted ultrasound signal, yields information about the condition of the patient's bone. Characteristics to be evaluated include, without limitation, frequency, amplitude and phase.

The complicated transformation of the ultrasound excitation which occurs as it propagates through the patient is not yet fully understood. Present indications are that for the patella, within the frequency spectrum of interest, the higher frequency components travel as a leakage mode through the soft tissue covering of the bone and that the lower frequency components propagate along a parallel path in the relatively dense bone. More particularly, with respect to the patella, the lower frequency signals appear to propagate in the relatively dense subcortical bone layer just beneath the anterior surface. This bone path sharply attenuates the high frequency content of the applied ultrasound pulse. For other bones, the transformation is not so well understood.

In the first embodiment of the invention (see FIGS. 3 and 4), the transducers are mounted on a digital caliper device, 38. The calipers are closed about the bony member to be evaluated, with the transducers in contact with the patient's surrounding skin. The coupling of ultrasound energy between the transducers and the tissue is facilitated by an impedance matching gell or other such material. As the excitation is being launched and received, the caliper automatically measures the distance travelled by the pulse (i.e., the separation between the opposing faces of the transducers), as indicated by block 8. After the transmission and excitation data have been recorded, a template signal is provided as indicated at 10, which is matched through a cross-correlation function to the signal corresponding to the excitation at the receiving transducer. Evaluation of the cross-correlation function permits filtering out the noise making up the baseline signal, thereby facilitating pinpointing the exact time of arrival of the pulse, block 12. Now, knowing both the elapsed time of pulse travel, from 12, and the distance travelled, from 8, the average velocity of the ultrasound pulse through the bone and minimal surrounding soft tissue may be computed, block 14.

Even at the kneecap, a normally bony area, some patients exhibit non-trivial amounts of soft tissue; therefore, it is beneficial to correct or adjust the velocity measurements to eliminate the effect of soft tissue, 16. According to the invention, a factor related to the patient's height and weight ratio can be used.

The velocity measurement may alternatively be adjusted, or corrected, with respect to the patient's soft tissue content according to a more sophisticated echo technique, described more fully in U.S. Pat. No. 4,361,154, identified above, the disclosure of which is incorporated herein by reference. This method takes advantage of the fact that a portion of the ultrasound energy reflects from the bone, as the signal crosses the interface between the soft tissue and the bone. It is possible to measure the thickness of the soft tissue covering the bone on each end of the ultrasound signal path by launching an ultrasound pulse from each transducer, and measuring the time until receiving a reflected echo pulse. This technique requires equipment capable of launching an ultrasound pulse from both transducers and of monitoring the excitation at both transducers. The speed of an ultrasound pulse travelling through soft tissue is known and is approximately 1,550 m/sec. Thus, examination of the record of the ultrasound echo transmission will give the time period during which the ultrasound pulse travelled through the soft tissue, reflected from the bone and came back to the launching transducer, for each transducer. Knowing the velocity during this travel, the path length may also be determined. This path length through the soft tissue may be subtracted from the total distance between the transducers, thus arriving at the distance travelled through the bone. Further, the time of transmission through the bone may also be computed, by subtracting from the time measured the period spent during transit through the soft tissue, as determined above.

The velocity measured between the two transducers may also be normalized with respect to the patient's soft tissue characteristics, by means of a factor produced by a standard "skin fold" test. According to the skin fold test, measurements with calipers are taken at several designated spots of a patient's body, to measure the amount of skin the soft tissue at the spots. Large amounts of data have been collected from the general populace, ranking persons according to a general "fleshiness" based on the skin fold tests. An index based on this test could also be used to normalize the velocity measured through the bone and soft tissue.

The adjustment for soft tissue, however generated, whether by height/weight or skin-fold reference, or echo technique, will be referred to in the following as a "soft tissue adjustment factor." Thus, from the absolute velocity measured, and the soft tissue adjusted factor, a soft tissue adjusted velocity is determined, step 18.

Figure 3:
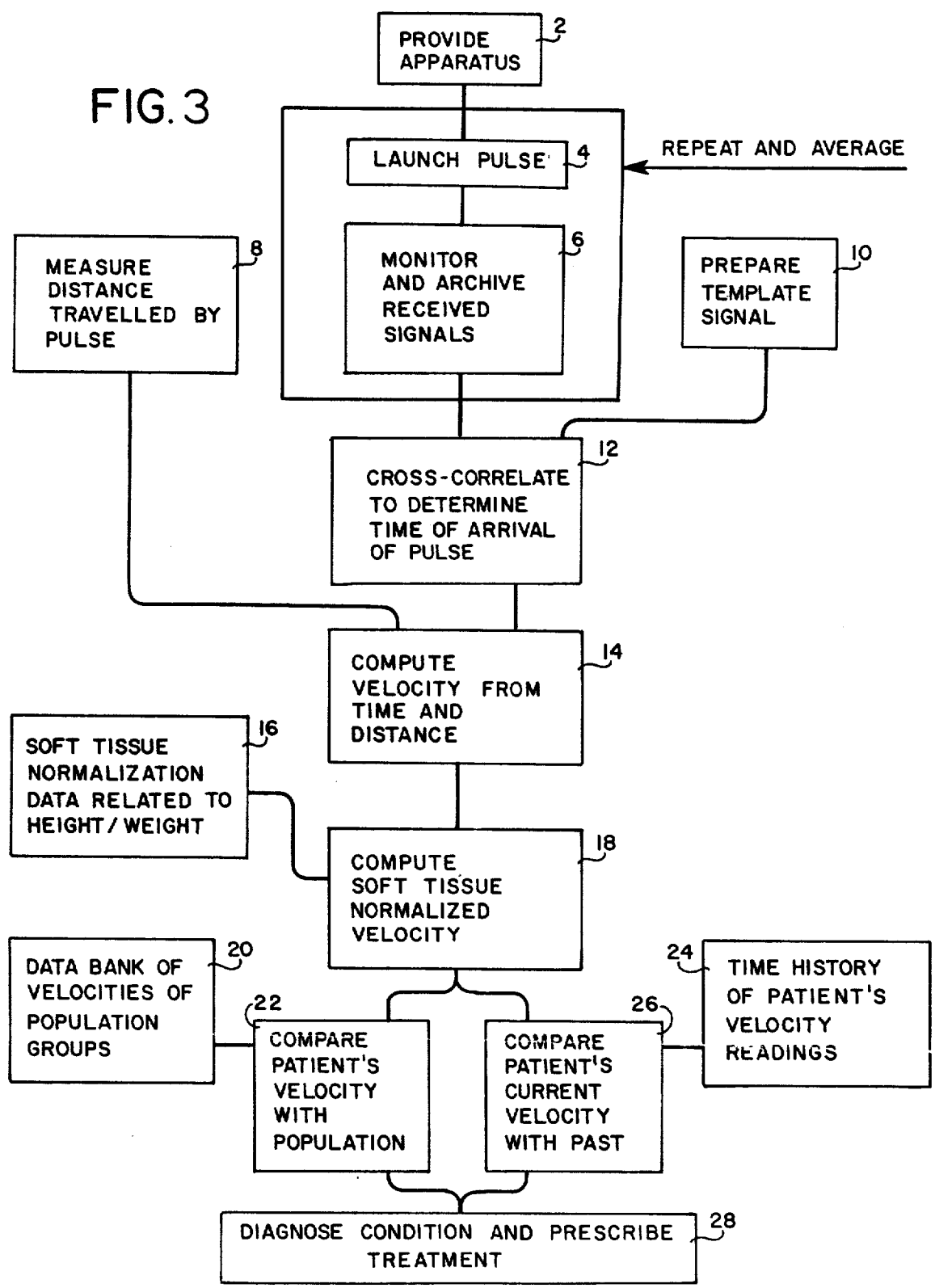
FIG. 3 is a flow chart outlining in greater detail the implementation of step 7 of FIG. 1 as a sequence of more specific steps according to a first embodiment of the method of the present invention.

The soft tissue adjusted velocity may be used in a number of ways, two of which are indicated in FIG. 3. First, the adjusted velocity may be compared (22) to entries in a data compilation of adjusted velocities gathered from a wide cross-section of the population (20). This data bank may be organized according to ranges of ages and other patient characterisitics (e.g, sex, race, ethnic group, etc ), and also according to known skeletal conditions. Thus, if the adjusted velocity of a 40-year-old woman falls within the standard range of known velocities for 40-year-old women in the population at large, it can be said with a reasonable certainty that this person has healthy bones. Conversely, if the adjusted velocity falls within the range normally associated with healthy 60-year-old women, there is a substantial probability of an abnormal condition and it would be wise to begin preventative and rehabilitative treatment.

An adjusted velocity may also be compared to previous and future measurements made with respect to the patient under examination, step 26. Under this scheme, measurements will be made for an individual over the course of years, step 24. Thus, significant change in ultrasound velocity will indicate a significant change in bone condition. Depending upon the direction of the change in bone condition, it will be possible to determine whether the patient's health is improving or deteriorating, step 28.

Figure 4:
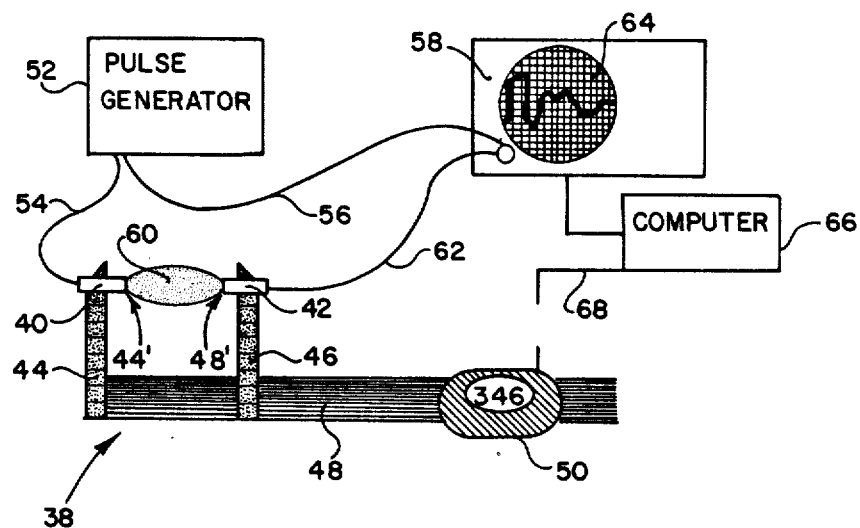
FIG. 4 shows a schematic representation of an apparatus that may be used to practice the method of both embodiments of the invention, though the caliper is unnecessary for the second embodiment.

With reference now to FIG. 4, a suitable apparatus for practice of this method will be described in detail. A sending transducer 40 and a receiving transducer 42 are provided. Each transducer (40 and 42) is capable of launching a broad band high frequency ultrasound pulse. Transducers manufactured by Panametrics Inc., 221 Crescent Street, Waltham, Mass. 02254, such as the Panametrics model A533S transducer, have been used with good results. The latter is represented as a 2.25 MHz transducer. 2.25 MHz is a desirable base frequency for several reasons. First, transducers capable of transmitting and receiving ultrasound at this frequency are relatively small, measuring approximately one-third of an inch in diameter Thus, they may conveniently engage parts of the patient's body. Secondly, the frequency must be high enough so that the sensitivity of the device will be able to resolve measurements of time at least as small as about $1 \times 10^{-6}$ seconds. This requires a frequency of at least 1 MHz. A higher frequency device has more ability to resolve time measurements than a lower frequency device. Unfortunately, if the frequency is too high, the amplitude of the signal received at the receiving transducer will be attenuated seriously due to reflection at boundary surfaces surrounding and within the bone. We have found that a base frequency of about 2.25 MHz provides a reasonable compromise between the competing concerns of sensitivity and transmitted amplitude. With reference to FIG. 2, the spectrum of the signal emitted by the above-described transducer is shown. It will be seen that the spectrum contains substantial energy components from about 100 kHz to about 3 MHz. This broad spectrum is desirable, as the signal transmitted through the bone has significant energy at frequencies in the neighborhood of 300 kHz, while the signal transmitted through soft tissue has significant energy at frequencies in the neighborhood of 2.5 MHz; thus, the transducer and signal generator 52 must be operable in both frequency ranges. Since these two transmissions (i.e., bone and soft tissue) are substantially independent, similar results may be achieved with narrow band transducers excited either by narrow band sources operating at separate frequencies or by a wide band source.

The transducers are mounted on an automatic electronic digital vernier caliper 38, manufactured by Fred V. Fowler Co., Inc., 66 Rowe Street, Newton, Mass. 02166, model name "Ultra-Cal." The vernier caliper has a stationary arm 44 and a movable arm 46. As the movable arm 46 moves along the support arm 48, the distance between the transducer faces 44' and 46' are displayed on the display 50. The workings of this caliper are unimportant to the disclosed invention, and an ordinary vernier caliper also could be used. However, in that case, manual reading and recording of the distance would have to be taken, and the distance would have to be read into the data processing equipment by hand.

In use, the sending transducer 40 and receiving transducer 42 are brought to bear upon opposite surfaces of a bony portion of the patient's body 60, preferably the kneecap. The pulse generator 52 generates a pulse of a duration of approximately $2 \times 10^{-6}$ seconds. This pulse is transmitted along electrical connection 54 to the launching transducer 40. Simultaneously, along electrical connection 56, a launch signal is transmitted to the data acquisition system 58, indicating the departure of the launched pulse. This latter signal is used by the signal processor to record the time of launch. For the data acquisition system, a Data 6000, manufactured by the Data Precision division of Analogics Corporation, Peabody, Mass., has been used with good results.

The pulse travels through the member being measured 60 and is received by the receiving transducer 42. The receiving transducer 42 emits signals that are electrically transmitted along lead 62 to the data acquisition system 59. These signals correspond to the ultrasound pulse received by the transducer 42.

The data acquisition system 58 is capable of storing the amplitude of the signals received by it, and displaying the time-varying amplitude upon a standard CRT display 64. The data acquisition system includes data computing means 66, shown schematically in FIG. 4. A signal representing the distance measured by the caliper 38, between the transducer faces 44' and 46', has been transmitted along electrical connection 68 to the computer 66, for use at a later step as described below.

Figure 5:
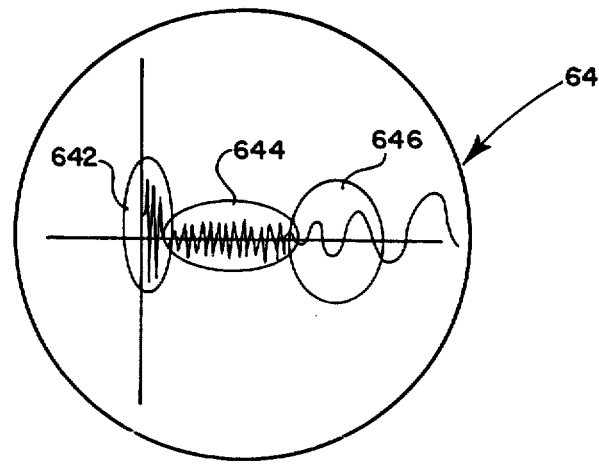
FIG. 5 shows a schematic representation of a typical plotting of the amplitude of the received excitation versus time, for one ultrasound pulse.

The next figure, FIG. 5, shows schematically a typical response received by the receiving transducer before the cross-correlation technique of "matched filtering," described below, has been applied. In FIG. 5, the display is represented by 64. The horizontal axis represents elapsed time. The time from the origin to the end of oval 644 is on the order of 15 to $20 \times 10^{-6}$ seconds. The vertical axis represents the amplitude of the signal received.

The portion of the signal indicated within the circle identified as 642 shall be referred to as the "main bang" and constitutes the record of the launched pulse. The portion of the signal roughly circumscribed by oval 644 is the base line noise received by the receiving transducer. The portion of the signal indicated by oval 646 represents the initial receipt by the receiving transducer of any signal passing through the bone and soft tissue as a result of the launched pulse. This received signal consists of two distinguishable components: a first arriving low frequency signal followed by a later arriving high frequency signal (which may also be termed a "received first distinguishable component" and a "received second distinguishable component"). It is good practice to average the amplitude of the received signals from a number (e.g., 16 or more) of separate, initial pulses. Random signals, such as noise, tend to average to zero.

As can be seen from the schematic representation in FIG. 5, it is difficult to determine precisely the time at which the signal 646 emerges from the baseline noise 644. Errors in determining the time of arrival by as much as $1 \times 10^{-6}$ seconds can result in an error in the velocity calculation of as much as 10 percent. Although measurements made with an error of this amount will be useful, it is, of course, highly desirable to eliminate (or, at least, minimize) this error to the extent possible.

Fortunately, an error correction method has been developed. This method is known as "matched filtering." It is described in full in various texts, such as Y. W. Lee, *The Statistical Theory of Communication*, published by Wiley in 1960. The error correction method is shown schematically in FIG. 6. In general, the baseline noise is filtered out of the display of the received signal, by signal averaging and cross-correlation. A template signal is provided that matches, to a significant degree, the shape of the averaged incoming first arrived signal received through the bone. As will be evident below, it is not necessary that the template be exactly identical to the leading edge of the received signal through the bone It must only be similar. The template may be obtained, for example, by taking an appropriate number of cycles (e.g., one-half a period) of the dominant "low-frequency" Fourier component received for that patient. Preferably, two template signals are used, one pertaining to transmission through the bone and the other pertaining to transmission through the soft tissue. The latter may be a standard signal since there is very little difference from one patient to another in the velocity of ultrasound through soft tissue or in the frequency response of the soft tissue It may be desirable to use different sampling intervals and/or sampling rates for the two different template signals in order to provide an appropriate number of sample points within the template.

Only a small portion of the signal, such as 180 degrees of one cycle, is retained. The cross-correlation function C(d) is defined as $$C(d) = \int_{-\infty}^{\infty} F(t) G(t - d) dt$$

Figure 6:
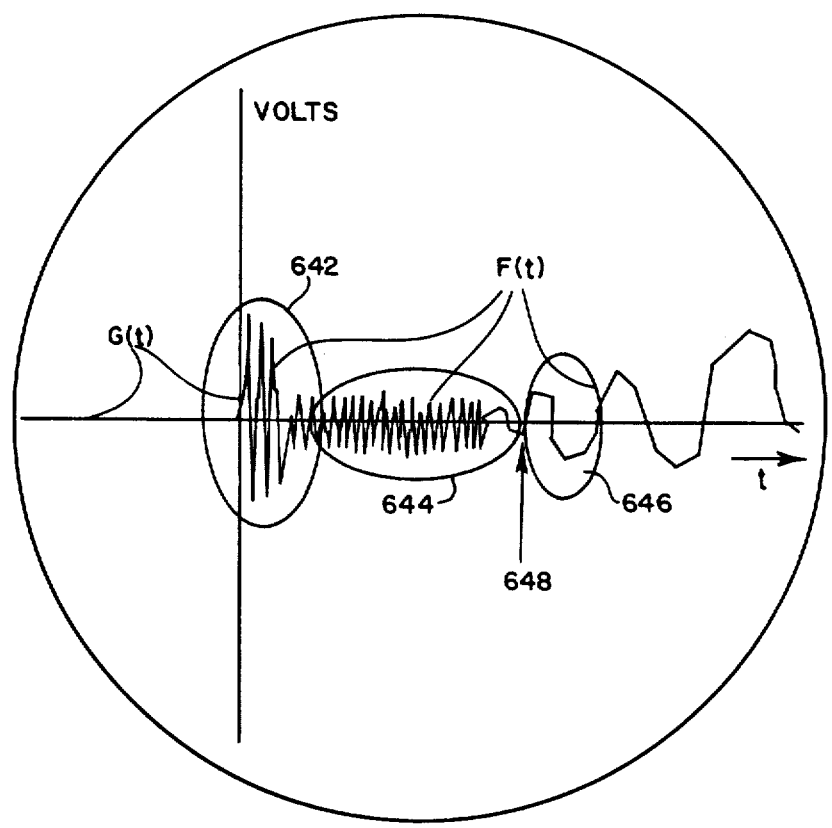
FIG. 6 schematically shows the method of "matched filtering;"

The function F(t) is the signal received by the receiving transducer as indicated in FIG. 6. The function G(t-d) is the template signal, which is non-zero only near the origin. In order to pinpoint the moment of arrival of the signal through the bone, the integral is performed as time ranges from zero to infinity. Then the first extremum of this integral is selected as "d" ranges from zero to infinity.

The time 648 at which the absolute value of C(d) exceeds a first maximum that exceed a threshold typical of artifact signals, is, except in one instance as explained below, the time that the signal first arrived. This occurs due to the following. Up until the initial receipt of the transmitted pulse, the function F(t) is made up of the rapidly oscillating signal of the main bang and the baseline (644). These signals oscillate in general at about 2 MHz. Conversely, the template signal appropriate for trabecular bone has a period of $3.3 \times 10^{-6}$ seconds and thus has a frequency of 300 Hz. Because the main bang and baseline noise vary from positive to negative, the integral of the product of the two functions F(t) and G(t-d) will be zero at all times of rapid oscillation. It is not until the transmitted pulse has arrived (time 648) that the product of the cross correlation function, template G(t-d) and F(t), which now is comprised largely by the signal from the transmitted pulse, beings to have a non-zero value. When the received signal most closely matches the template, the product will be at a maximum. A corresponding situation pertains if the main bang, instead of having the wideband waveform of FIG. 2, comprises a plurality of separate signals.

As was mentioned above, there will be some instances where the maximum of the cross correlation function will not coincide with the arrival of the first arrived pulse. This will be in those cases where the amplitude of the first arrived pulse is of an opposite sign with respect to the template; for instance, if the template has been chosen from a positive segment of a bone signal, while the first arriving signal is negative. These cases may be easily identified by noting that the cross-correlation function will have a relatively large negative excursion before the maximum value. In this case, the arrival of the first arriving pulse is indicated at the large negative excursion. More precise measurements may be made by performing two cross correlations, one with a positive template and one with a negative template, and then choosing the appropriate record to archive based on the observed results. Or the cross correlation function may be squared, in which case the maximum of the resulting function will coincide with the arrival of the first arrived pulse. Optionally, it may be desirable to perform the matched filtering process more than once, combining the template G(t-d) with C(t) to produce C'(d).

This type of signal matching can be accomplished automatically by the data acquisition system identified above.

It should be noted that this matched filtering need not be done at the time of patient examination, and may be performed later, on stored data. After the cross-correlation has been maximized, and the elapsed time for the signal propagation has been determined, the velocity may be computed by dividing the distance between the transducers measured earlier, by the elapsed time.

Once the average velocity through the path between the transducers has been determined, it is beneficial to eliminate the effect of the passage of the ultrasound pulse through the soft tissue surrounding the bone. This is because the time for transit of the pulse from one transducer to the other includes time during which the ultrasound pulse is passing through the bone, and also time during which the ultrasound pulse is passing through soft tissue surrounding the bone. Further, the distance travelled by the ultrasound pulse includes the distance through the bone, and also the distances through the layers of soft tissue on both sides of the bone. Failure to account for this transit delay through the soft tissue reduces the accuracy of the velocity determination made by simply dividing the distance travelled by the time.

Experiments have shown that the kneecap is a very good spot on the human body to examine the condition of trabecular bone and also to test for osteoporosis. The kneecap is a part of the body substantially free of soft tissue. Further, the kneecap is largely made up of trabecular bone, the type of bone in which osteoporotic effects are felt earliest and most severely. We believe the tibial crest is also a good location on the human body at which to examine the condition of cortical bone.

Despite the advantages of measuring at the patella and tibial crest, as has been mentioned above, the presence of significant amounts of soft tissue there does influence the results to some extent. Therefore, it is beneficial to correct the measured velocity by adjusting for the patient's specific soft tissue condition. As has been mentioned above, these methods include echo techniques, skinfold tests and height and weight comparison. The velocity computed according to either method shall be referred to as the "adjusted bone velocity."

Once the adjusted bone velocity has been determined, this value may be used to evaluate the patient's skeletal condition. This may be done by comparing the adjusted bone velocity to adjusted bone velocities obtained from a large cross-section of the general population. Ideally, the general data base of adjusted bone velocities is grouped in ranges of ages and other characteristics, so that a typical velocity for a healthy person of a certain age and characteristic will be known. The data base should also include, for each age or age group, a series of velocities corresponding to a spectrum of bone density conditions, from more porous than normal to more dense than normal. By comparing the patient's adjusted bone velocity to the spectrum of adjusted velocities for their age, their relative bone condition may be determined.

Further, in conditions where an individual is either suspected of being osteoporotic, or is undergoing treatment for osteoporosis, specific measurements may be compared to previous measurements made of the same patient. These measurements are known as "serial measurements." Thereby, their progress or deterioration may be charted and treated.

Figure 7:
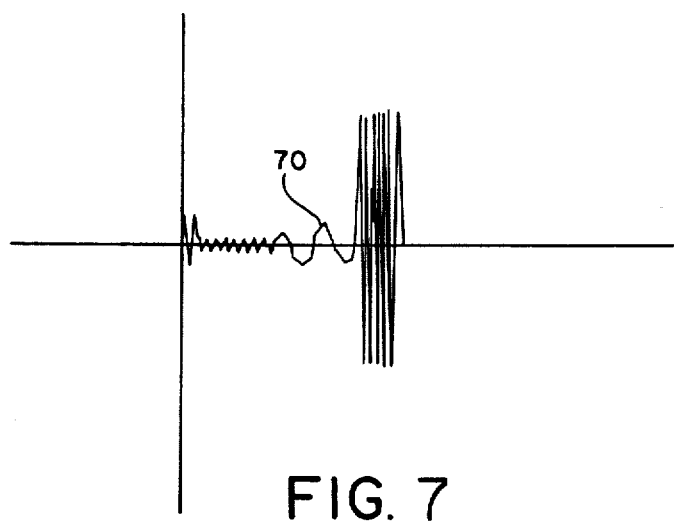
FIG. 7 shows schematically the first arriving waveform after passing through healthy bone.
Figure 8:
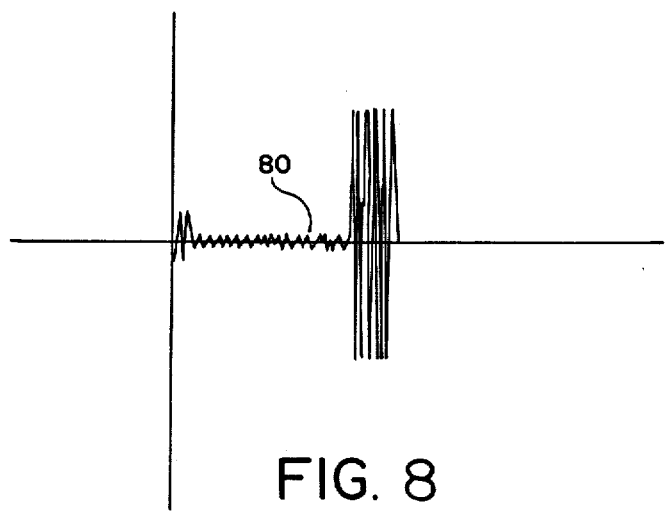
FIG. 8 shows schematically the first arriving waveform after passing through osteoporotic bone.

It is also a feature of the method of the present invention to evaluate the patient's bone condition on the basis of the shape of the amplitude of the transmitted waveform. The shape of the waveform of the received ultrasound pulse contains valuable information regarding the density and condition of the patient's skeleton. We have observed that with healthy patients, the shape of the signal through the patella that first arrives at the receiving transducer may be roughly characterized as having a first portion of well-defined oscillations more than twice the rms baseline noise with a frequency of about 300 kHz, followed by very high amplitude, high frequency oscillations near 2.5 MHz. FIG. 7 schematically shows this type of bone signal. In FIG. 7, the signal that has passed through the healthy bone ("the healthy signal") is labeled "70". In FIG. 8, a signal that has passed through the diseased bone ("diseased signal") is labeled "80". As can be seen from this figure, the diseased signal first arrives with virtually no well-defined oscillations, beginning almost immediately with the high frequency, high amplitude oscillations.

The mechanics underlying this variation in waveform shape, and the significance of the waveform shape, are not well understood. It is believed that the well-defined low frequency oscillations evidence longitudinal, or compression waves, while the high frequency, high amplitude oscillations are transverse, or shear waves. Longitudinal waves result from oscillation of the medium in a direction parallel to the direction of propagation, while shear waves are evidence of oscillation perpendicular to the direction of propagation. Longitudinal waves generally travel faster than shear waves. However, it is believed that in osteoporotic bone, the pathways for travel of compressive ultrasonic pulses through trabecular bone portions are more restricted and also interrupted by the termination of trabecular formations and by interposed pockets of fluid. These discontinuities in the medium change the elasticity of the bone and cause the dissipation of energy embodied in the ultrasound pulse: consequently, the amplitude of the compressive ultrasound pulse is reduced in the osteoporotic patient.

Additionally, the transducers may be arranged to launch (i.e., transmit) head waves and shear waves. The speed of propagation of these waves, and the further waves they induce, provides still more information on the state and properties of the bone intermediate the transducers. A given bone may be excited in many different modes; the goal is to find and use those modes for which transmission is particularly sensitive to bone characteristics of interest (e.g., porosity, density and elasticity).

To generate these other types of waves, the launching and receiving transducers may be arranged in ways other than the arrangement of FIG. 4. Oblique or normal transducer dispositions may be desirable; for example, to generate head waves, the transducers are spaced apart on the same side of the bone, both facing the bone. Consequently, the present invention is not intended to be limited to the arrangement of FIG. 4 (i.e., parallel, spaced apart transducers, facing each other).

When a continuous-wave signal is injected instead of a pulse signal, the signal processing must be modified. Appropriate signal processing is known to those skilled in the art, as indicated, for example, in R.B. Ashman et al , "A Continuous Wave Technique for the Measurement of Elastic Properties of Cortical Bone," *Journal of Biomechanics*, Vol. 17, pp. 349-361 (1984), the disclosure of which is hereby incorporated by reference.

In a second embodiment of the invention, we have taken advantage of the foregoing observation that the low frequency oscillations and the high frequency oscillations arrive at different times, to devise a measurement technique which is independent of transducer separation and thus does not require measurement of that separation. As stated above, in this embodiment, digital caliper 38 may be omitted, although some mechanism should still be used for supporting and positioning the transducers and holding them steady against the patient; the same caliper can be employed for this purpose but its digital output is not needed. Otherwise, the apparatus is the same as that shown in FIG. 4. The primary difference between this and the prior embodiment thus lies not in the hardware, but, rather, in the processing of the signals arriving at receiving transducer 42.

Figures 9, 11:
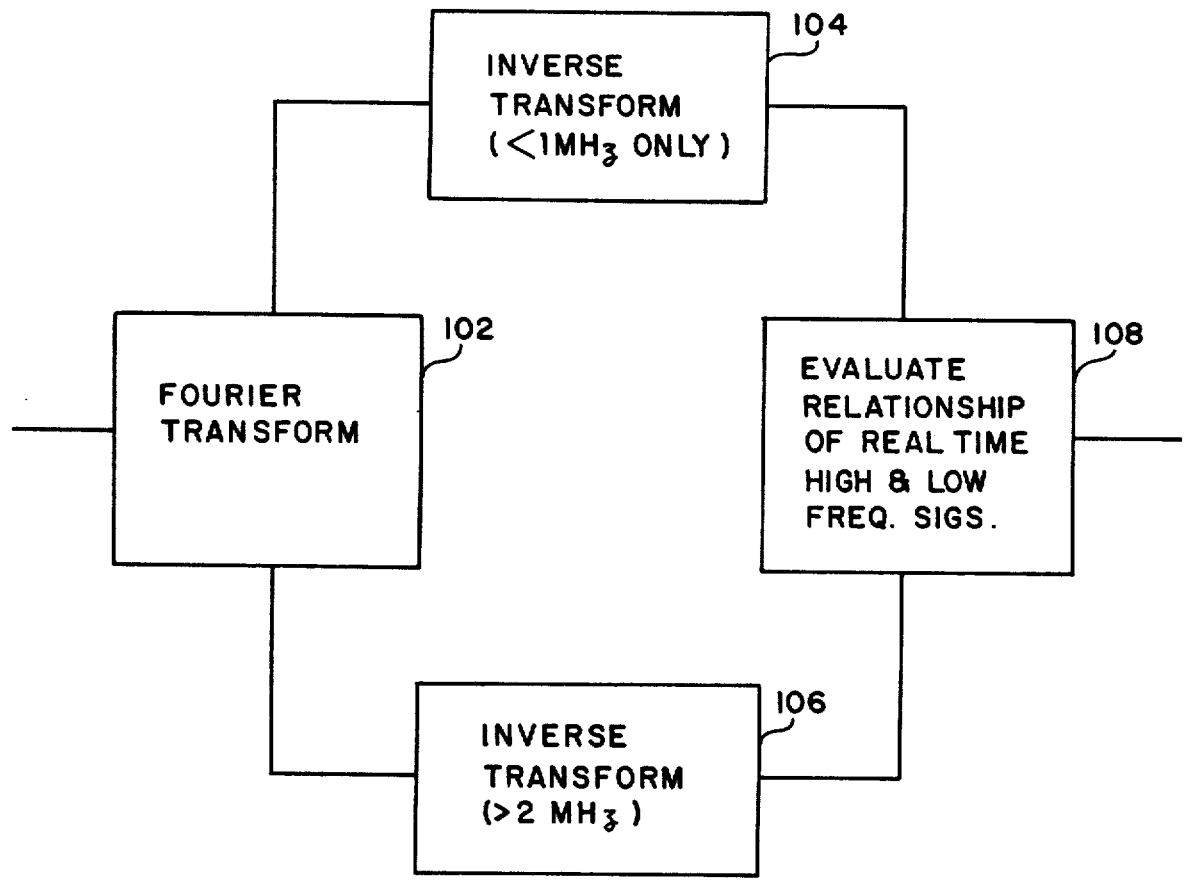
FIG. 9 is a flow chart outlining in greater detail the implementation of step 7 of FIG. 1 as a sequence of more specific steps according to a second embodiment of the method of the present invention.
FIG. 11 is a table listing exemplary data obtained by the method of FIG. 9.

This processing is illustrated in FIG. 9. First, a Fourier transform of the received signal is calculated (step 102) using conventional techniques. Next, two inverse transforms are made, one omitting all frequencies above 1 MHz (step 104) and one omitting all frequencies below 2 MHz (step 106). These inverse transforms yield a time-domain low frequency signal and a time-domain high frequency signal, respectively, illustrated at 112 and 114 in FIGS. 10A and 10B. (These two signals may also be referred to as a received first and second distinguishable component of the received signal.) Alternatively, the step of making the first of the two inverse transforms may be omitted.

In band-limiting the Fourier-transform to generate the inverse transforms, square windows have been employed, due to the limitations of the signal processing equipment. Better results might be obtained, of course, with a Hamming window or a Blackman window, in order to reduce artifacts introduced into the inverse transforms by the windowing (i.e., band-limiting) process.

Due to the separation between the frequencies of the time-domain high frequency signal and the time-domain low frequency signal, it is apparent that equivalent results can be obtained by exciting the bone with not just one broadband pulse, but rather, with two or more band-limited pulses emitted either simultaneously or in succession. That is, the low frequency response and the high frequency response can be measured at different times or at the same time. Filtering (analog or digital) may be used to separate the received signals into their "tissue" and "bone" components. This can simplify the signal processing, as the transform approach can be avoided while obtaining substantially equivalent results; a variety of spectral estimation techniques may be employed as alternatives to such exemplary processing.

The relationship between selected characteristics of the time-domain high frequency signal and the time-domain low frequency signal is evaluated (step 108) to provide an indicator of bone condition. This evaluation can involve various measurements. For example, taking the ratio of the first arrival times of the low frequency pulse component 112 and the high frequency pulse component 114 is believed to yield a good diagnostic predictor of osteoporosis. FIG. 11 shows in tabular form the average of this ratio and the standard deviation of the distribution for a sampling of 47 women who had been previously classified in three categories: osteoporotic, normal and athletic (i.e., runners). Application of the well-known "t-distribution" formula to this data indicates that the foregoing ratio distinguishes an osteoporotic patient group from a "normal" patient group to a 98% level of confidence. Thus, the calculated ratio can be compared with one or more predetermined threshold values to place the test results for the patient into a category associated with a corresponding probability that the patient has an abnormal bone condition. The various threshold values (i.e., conditional probability level ranges) need not be the same for all patients. Different threshold values may be used for patients of different age, sex or race, or possessing other characteristics. Similarly, different levels of confidence or conditional probability may be established for the rate of change of the predictor for measurements taken on the patients over a period of time. Thus, a patient whose predictor changes monotonically at a rate of x% per year may be said to have a y% chance of being or becoming osteoporotic. The establishment of appropriate confidence level groupings and threshold values therefor is a straightforward exercise simply requiring testing of a large number of patients and conventional statistical analysis of the results.

As an alternative to use of the ratio of first arrival times, we have also found on a small sampling that good results are obtained by using as an evaluator of bone condition the frequency-dependent gain function of the power spectrum of the received signal divided by the power spectrum of the excitation. However, since there may be zeroes in the denominator, it is advisable, instead of performing a simple division, to instead generate a function, using existing methods, which approximates the deconvolution of the low-frequency component by the high-frequency component while compensating for noise and for such zeroes. Such a function might be obtained, for example, by Weiner filtering. Or the gain function may be limited to the low-frequency portion of each (e.g., that part below 1 MHz). Both the area under these gain functions and their peak values appear to be useful indicators of bone condition.

Taking further advantage of the fact that the low-frequency components and high-frequency components of the acoustic signal arrive at different times, it is also possible to generate those high-frequency and low-frequency components separately, such as by launching a succession of pulses, some with lower frequency components and others with higher-frequency components. With this possibility in mind, the singular "pulse" as used above should be understood to include the possibility of at least one pulse of lower frequency content and at least one pulse of higher frequency content.

The foregoing description of the method should be taken as illustrative and not limiting. The kneecap has been identified as the preferred testing site on the human body for the evaluation of trabecular bone and diagnosis or monitoring of osteoporosis. The tibia provides useful results in examining compact bone Tibial results with respect to observing osteoporosis are limited to some extent, because the tibia is largely made up of cortical bone, rather than trabecular bone. Therefore, the effects of osteoporosis are not felt as early in the tibia as in trabecular bones, such as the kneecap and the spinal cord. Further, although the method has been described in connection with diagnosing osteoporosis, it may also be used to diagnose other bone conditions. For example, it may be used to diagnose periodontal bone loss which contributes to periodontal disease, and to assess the healing of fractures.

The invention is also applicable to evaluation of animal bone conditions, but the frequency spectrum of the applied acoustic excitation may have to be varied to adjust to the animal. It may also be desirable to modify the frequency spectrum when evaluating conditions other than osteoporosis. Various other alterations, modifications and improvements will thus be obvious and will occur to those skilled in the art. Moreover, the invention may be useful also for invasive testing of bones. For this purpose, transducer-tipped needles may be placed in direct contact with a bone to be studied. When this is done, of course, there is no need to make adjustments for soft tissue.

The invention is therefore intended to be limited only by the following claims and equivalents thereto, and not by the foregoing examples

What is claimed is:

1. A method of assessing the condition of a bony member of a patient comprising the steps of:
   a. launching into the patient an ultrasound signal having at least one component at a frequency greater than a first predetermined frequency and at least one other component at a frequency less than a second predetermined frequency, such signal being launched into a first position proximate the surface of a bony member which may be surrounded by minimal soft tissue;
   b. proximate a second position on the surface of said bony member, monitoring the ultrasound spectrum inclusive of said frequencies and generating electrical signals (termed "received signals") corresponding to the energy in said monitored ultrasound spectrum;

c. extracting from the received signals the components thereof at frequencies greater than the first predetermined frequency, thus providing a time-domain high frequency signal, and extracting the components thereof at frequencies less than the second predetermined frequency, thereby providing a time-domain low frequency signal; and d. comparing the time-domain high frequency signal to the time-domain low frequency signal, to provide an indicator of the condition of the bony member.

2. The method of claim 1 wherein the bony member is the patella.

3. The method of claim 1 wherein the first and second predetermined frequencies are the same frequency.

4. The method of claim 1 the first and second predetermined frequencies are different frequencies.

5. The method of claim 1 wherein the step of comparing the time-domain high frequency signal to the time-domain low frequency signal further comprises the step of taking the ratio of the first arrival time of the time-domain high frequency signal and the first arrival time of the time-domain low frequency signal.

6. The method of claim 1 wherein the step of comparing the time-domain high frequency signal to the time-domain low frequency signal further comprises the step of generating, as a function of frequency, a function of the power spectra of such signals.

7. The method of claim 6 including the further step of comparing the area under such function with at least one threshold value and responsive to such comparison, identifying a probability that the patient's bone condition is abnormal.

8. The method of claim 7 wherein the abnormal bone condition is osteoporotic.

9. The method of claim 8 wherein the bony member is a patella.

10. The method of claim 9 wherein the step of comparing the time-domain high frequency signal to the time-domain low frequency signal further comprises the step of generating a ratio of the first arrival time of the time-domain high frequency signal and the first arrival time of the time-domain low frequency signal.

11. The method of claim 9 wherein the step of comparing the time-domain high frequency signal to the time-domain low frequency signal further comprises generating a function of the power spectra of such signals.

12. The method of claim 11 including the further step of comparing the area under such function with at least one threshold value and responsive to such comparison, identifying a probability that the patient's bond condition is abnormal.

13. The method of claim 11 including the further step of comparing the peak amplitude of such function with at least one threshold value and responsive to such comparison, identifying a probability that the patient's bone condition is abnormal.

14. The method of claim 9 wherein the step of comparing comprises generating a frequency-dependent function approximating the deconvolution of the time-domain low frequency signal by the time-domain high frequency signal.

15. The method of claim 10 wherein the step of extracting from the received signals the components thereof at frequencies greater than and less than said predetermined frequencies comprises the further steps of:

(1) computing a Fourier transform of the received signals;

(2) generating a first inverse transform from the Fourier transform data, omitting all frequencies below the first predetermined frequency, to provide the time-domain high frequency signal; and (3) generating a second inverse transform from the Fourier transform data, omitting all frequencies above a second predetermined frequency, to provide the time-domain low frequency signal.

16. A method of assessing the condition of a bony member of a patient comprising the steps of:

a. launching into the patient an ultrasound signal containing energy components at frequencies in a spectrum from about 100 kHz to about 3.0 MHz, such pulse being launched at a first position proximate the surface of a bony member which is surrounded by minimal soft tissue;

b. proximate a second position on the surface of said bony member, monitoring said ultrasound spectrum, and generating electrical signals, termed "received signals" corresponding to the energy in said monitored ultrasound spectrum;

c. extracting from the received signals the components thereof at frequencies greater than a first predetermined frequency, to provide a time-domain high frequency signal, and the components thereof at frequencies less than a second predetermined frequency, to provide a time-domain low frequency signal; and d. comparing the time-domain low frequency signal to the launched ultrasound signal, to provide an indicator of condition of the bony member.

17. The method of claim 16 wherein the first and second predetermined frequencies are different frequencies.

18. The method of claim 16 wherein the first and second predetermined frequencies are different frequencies.

19. The method of claim 16 wherein the step of comparing the time-domain low frequency signal to the ultrasound signal further comprises the step of generating a gain function.

20. The method of claim 19 including the further step of comparing the area under such gain function with at least one threshold value and responsive to such comparison, identifying a probability that the patient's bone condition is abnormal.

21. The method of claim 20 wherein the abnormal bone condition is osteoporotic.

22. The method of claim 21 wherein the bony member is a member of the group consisting of the patella, the tibia, the maxilla and the mandible.

23. The method of claim 16 wherein the step of extracting from the received signals the components thereof at frequencies greater than and less than said predetermined frequencies comprises the further steps of:

(1) computing a Fourier transform of the received signals;

(2) generating a first inverse transform from the Fourier transform data, omitting all frequencies below the first predetermined frequency, to provide the time-domain high frequency signal; and (3) generating a second inverse transform from the Fourier transform data, omitting all frequencies above a second predetermined frequency, to provide the time-domain low frequency signal.

24. The method of claim 23 wherein the step of comparing the time-domain low frequency signal to the ultrasound signal further comprises the step of generating a gain function of such signals.

25. The method of claim 24 including the further step of comparing the area under such gain function with at least one threshold value and responsive to such comparison, identifying a probability that the patient's bone condition is abnormal.

26. The method of claim 24 including the further step of comparing the peak amplitude of such gain function with at least one threshold value and responsive to such comparison, identifying a probability that the patient's bone condition is abnormal.

27. The method of claim 16 wherein the step of comparing the time-domain low frequency signal to the ultrasound signal further comprises the step of comparing the relative phase of the time-domain high frequency signal to the relative phase of the ultrasound signal and, responsive to such comparison, identifying a probability that the patient's bone condition is abnormal.

28. A method of accessing the condition of a bony member of a patient comprising the steps of:
   a. launching into a first position proximate the surface of a bony member of the patient an ultrasound signal, such bony member being surrounded by minimal soft tissue;
   b. at a second position proximate the surface of said bony member, monitoring the spectrum of the ultrasound signal, and generating electrical signals corresponding to the energy in said monitored spectrum, each such electrical signal having a waveform associated therewith;
   c. said first and second positions substantially opposing each other on the surface of the bony member;
   d. comparing with a catalog of sets of waveform characteristics from a representative sample of the general public including for each age range a spectrum of bone conditions, at least one selected waveform characteristic of the generated electrical signals;
   e. selecting from said catalog that set of waveform characteristics which most closely matches the at least one selected waveform characteristic of the generated electrical signals; and
   f. determining the condition of the patient's bony member by comparing the age and bone condition represented by the matched catalog set of waveform characteristics with the patient's age.

29. The method of claim 28 wherein the ultrasound signal contains energy components at about 300 kHz.

30. The method of claim 29 wherein the ultrasound signal contains energy components from about 100 kHz to about 3 MHz.

31. The method of claim 28 wherein the waveform characteristic of the generated electrical signals is a gain function of the energy in the monitored spectrum relative to the ultrasound signal.

32. The method of claim 31 wherein the waveform characteristic of the monitored acoustic excitation is a feature of the gain function.

33. A method for evaluating the bone condition of a patient comprising the steps of:
   a. providing an apparatus including (i) first transducer means for launching a broad band acoustic signal, said first transducer means having a launching face; (ii) second transducer means for monitoring excitation in said frequency range, said second transducer means having a receiving face; (iii) positioning means for locating the launching face of the first transducer means and the receiving face of the second transducer means on opposite sides of a bony member of the patient, said bony member possibly being surrounded by soft tissue; (iv) signal generator means for exciting the first transducer means to launch an acoustic signal in said range; (v) a data acquisition system electronically connected to said signal generator means and to said second transducer means, said data acquisition system being capable of recording signals corresponding to the time variation of acoustic excitation at the second transducer means; and (vi) electronic data computation means for processing the recorded data;
   b. generating an acoustic signal with said signal generator and launching said acoustic signal from said launching transducer means into the bony member;
   c. monitoring acoustic excitation at the second transducer means and sending to the data acquisition system a signal corresponding to the monitored excitation;
   d. recording the history of the monitored excitation with respect to time, with the data acquisition system;
   e. providing an electronic template signal for comparison with the recorded time-varying history of the monitored excitation;
   f. maximizing a cross-correlation function between the signal corresponding to the monitored excitation and the template signal, to minimize the effect of noise in obscuring the record of the time of arrival at the second transducer means of the acoustic signal;
   g. determining the time of arrival of the acoustic signal response at the receiving transducer means, and from said time and the time of pulse launching, the duration of travel of the acoustic signal through the bone and soft tissue;
   h. measuring the distance through which the acoustic signal travels between the first and second transducer means;
   i. computing the velocity of the acoustic signal through the bony member and surrounding soft tissue by dividing the measured distance by the computed arrival time;
   j. normalizing the velocity with respect to the patient's soft tissue characteristics, by applying an appropriate soft tissue normalization factor;
   k. comparing the normalized velocity to a statistical representation of normalized velocities for different groups of the population, grouped according to their age and bone condition; and
   l. responsive to such comparison, indicating the bone condition of the patient.

34. The method of claim 33 wherein the acoustic signal has energy components in the frequency range from about 100 kHz to about 3 MHz.

35. The method of claim 33 or claim 34 wherein steps b, c, and d are repeated for a plurality of acoustic signals, and further including the step of averaging the monitored excitation responsive to the plurality of acoustic signals, and wherein the recorded history of monitored excitation comprises the history of the averaged monitored excitation and the step of determining the time of arrival of the acoustic signal response at the receiving transducer means comprises determining the time of arrival of the averaged response to the acoustic signals.

36. The method of claim 33 or claim 34 wherein the evaluated bone condition is osteoporosis.

37. The method of claim 33 or claim 34 wherein the acoustic signal comprises at least one pulse.

38. The method of claim 37 wherein the evaluated bone condition is osteoporosis.

39. The method of claim 33 or claim 34 wherein the acoustic signal is a change in a parameter of a continuous wave signal.

40. The method of claim 39 wherein said parameter is the phase of the continuous wave signal.

41. The method of claim 40 wherein the ultrasound signal is a continuous-wave signal and the launching of the ultrasound signal corresponds to changing a parameter of the continuous-wave signal.

42. The method of claim 40 wherein the steps of launching an ultrasound signal and determining the transit time are repeated a plurality of times and further including the step of determining the average of the compensated velocities for such plurality of ultrasound signals.

43. The method of claim 42 wherein the ultrasound signal comprises at least one pulse.

44. The method of claim 43, where said bony member is a member of the group consisting of the patella, the tibia, the maxilla and the mandible.

45. The method of claim 42 wherein said step of determining the patient's bone condition comprises the further steps of:
 (1) generating a template signal;
 (2) generating a cross-correlation function between the template signal and the averaged signals corresponding to the monitored excitation; and
 (3) evaluating said cross-correlation function to determine the time at which the ultrasound signal arrived at the second surface of the bony member.

46. The method of claim 45 wherein said step of determining the average of the compensated velocities comprises the further steps of:
 (1) measuring physical characteristics of the patient to determine a soft tissue adjustment factor; and
 (2) compensating for the effect of the soft tissue by adjusting the average pulse transit time through the bone and soft tissue by the soft tissue adjustment factor.

47. The method of claim 46 wherein the step of determining the patient's bone condition from the average of the compensated velocities further comprises the step of comparing the average of the compensated velocities to data representing measurements of average velocity through the bone for persons of the same age as the patient, such data including a wide spectrum of bone conditions.

48. The method of claim 41 wherein the step of determining the patient's bone condition from the average of the compensated velocities comprises the steps of:
 (1) recording, for different tests of the same patient over a period of time, the average of the compensated velocities;
 (2) comparing the average of compensated velocities from later tests with the average of compensated velocities from earlier tests; and
 (3) correlating a positive change in such average with respect to time with an improvement in bone condition, and a negative change in such average with respect to time with a deterioration in bone condition.

49. The method of claim 42, wherein the bone condition examined is osteoporosis.

50. The method of claim 49, wherein the bony member is a member of the group consisting of the patella and the tibia.

51. The method of claim 42 wherein the bone condition examined is periodontal bone disease.

52. The method of claim 51, wherein the bony member is a member of the group consisting of the mandible and the maxilla.

53. A method of assessing the bone condition of a patient comprising the steps of:
 a. launching into a first position proximate the surface of a bony member of the patient an ultrasound signal having a spectrum containing energy in the frequency range of about 100 kHz to about 3 MHz, such bony member being surrounded by minimal soft tissue;
 b. at a second position proximate the surface of said bony member, monitoring acoustic excitation due to said ultrasound signal, generating electrical signals corresponding to said excitation and recording such signals with the data acquisition system;
 c. measuring the distance between the first and second positions;
 d. determining the transit time of the ultrasound signal from the first position to the second position;
 e. responsive to said measuring step and said transit-time-determining step, determining the velocity of the ultrasound signal components travelling through the bony member and surrounding minimal soft tissue;
 f. computing from such velocity a compensated velocity adjusted to account for the effects of signal propagation through soft tissue surrounding the bony member; and
 g. determining the patient's bone condition from the compensated velocity.

54. The method of claim 53 wherein the ultrasound signal comprises at least one pulse.

55. The method of claim 54 wherein the ultrasound signal comprises a first portion having energy in a first part of said frequency range and a second portion having energy in a second part of said frequency range.

56. The method of any of claims 40–55 wherein said parameter is the phase of the continuous wave signal.

57. Apparatus for evaluating the condition of a bony member of a patient comprising:
 a. means for launching into the patient at a first position proximate a bony member transdermally, for transmission through such bony member and any surrounding soft tissue, an ultrasound signal containing energy components in an ultrasound spectrum from about 100 kHz to about 3.0 MHz;
 b. means for monitoring the spectrum of ultrasound signals arriving at a second position proximate such bony member, and for generating electrical signals (termed "received signals") corresponding to the energy in said monitored ultrasound spectrum;

c. means for extracting from the received signals (i) the components thereof at frequencies greater than a first predetermined frequency and providing a time-domain high frequency signal, and (ii) the components thereof at frequencies less than a second predetermined frequency and providing a time-domain low frequency signal; and d. means for comparing the time-domain high frequency signal to the time-domain low frequency signal to provide an indicator of the condition of the bony member.

58. The apparatus of claim 57 wherein the second position and first position substantially oppose each other on opposite sides of the bony member.

59. The apparatus of claim 57 wherein the means for comparing the time-domain high frequency signal to the time-domain low frequency signal generates the ratio of the first arrival time of the time-domain high frequency signal and the first arrival time of the time-domain low frequency signal.

60. The apparatus of claim 57 wherein the means for comparing the time-domain high frequency signal to the time-domain low frequency signal generates a frequency-dependent function of the power spectra of such signals.

61. The apparatus of claim 60 wherein the means for comparing compares the area under such function with at least one threshold value and responsive to such comparison, to identify a probability that the patient's bone condition is abnormal.

62. The apparatus of claim 60 wherein the means for comparing compares the peak amplitude of such function with at least one threshold and responsive to such comparison, to identify a probability that the patient's bone condition is abnormal.

63. The apparatus of claim 57 wherein the means for extracting from the received signals the components thereof at frequencies greater than and less than said first and second predetermined frequencies further comprises:

(1) means for computing a Fourier transform of the received signals, (2) means for generating a first inverse transform from the Fourier transform, omitting therefrom all frequencies below the first predetermined frequency and providing the time-domain high frequency signal, and (3) means for generating a second inverse transform from the Fourier transform, omitting all frequencies above the second predetermined frequency and providing the time-domain low frequency signal.

64. The apparatus of claim 63 wherein the means for comparing the time-domain high frequency signal to the time-domain low frequency signal includes means for computing a ratio of the first arrival time of the time-domain high frequency signal and the first arrival time of the time-domain low frequency signal.

65. The apparatus of claim 63 wherein the means for comparing the time-domain high frequency signal to the time-domain low frequency signal includes means for generating a frequency-dependent function of the power spectra of such signals.

66. The apparatus of claim 65 wherein the means for comparing is further adapted to compare the area under such function with at least one threshold value and responsive to such comparison, to identify a probability that he patient's bone condition is abnormal.

67. The apparatus of claim 65 wherein the means for comparing is further adapted to compare the peak amplitude of such function with at least one threshold and responsive to such comparison, to identify a probability that the patient's bone condition is abnormal.

68. Apparatus for evaluating the condition of a bony member of a patient comprising:

a. means for launching into the patient, for transmission through a bony member and any surrounding soft tissue, an ultrasound signal containing energy components in an ultrasound spectrum from about 100 kHz to about 3.0 MHz;

b. means for monitoring energy in said ultrasound spectrum arriving at a second surface of said bony member, substantially opposing said first surface, and for generating electrical signals (termed "received signals") corresponding to the energy in said monitored ultrasound spectrum;

c. means for extracting from the received signals the components thereof at frequencies less than a predetermined frequency and providing a time-domain low frequency signal; and d. means for comparing the time-domain low frequency signal to the launched ultrasound signal to provide an indicator of condition of the bony member.

69. The apparatus of claim 68 wherein the means for comparing includes means for generating a gain function comparing the time-domain low frequency signal to the launched ultrasound signal.

70. The apparatus of claim 68 wherein the means for comparing includes means for generating a gain function of the power spectra of the time-domain low frequency signal and the launched ultrasound signal.

71. The apparatus of claim 70 wherein the means for comparing further includes means for comparing the area under the gain function with at least one threshold value and responsive to such comparison, identifying a probability that the patient's bone condition is abnormal.

72. The apparatus of claim 70 wherein the means for comparing includes means for comparing the peak amplitude of the gain function with at least one threshold and responsive to such comparison, identifying a probability that the patient's bone condition is abnormal.

73. The apparatus of claim 63 wherein the means for extracting from the received signals the components thereof at frequencies less than a predetermined frequency further comprises:

(1) means for computing a Fourier transform of the received signals, and (2) means for generating an inverse transform from the Fourier transform data, omitting all frequencies above the predetermined frequency, to provide the time-domain low frequency signal.

74. The apparatus of claim 68 wherein the ultrasound signal is a pulse.

75. The apparatus of claim 68 wherein the ultrasound signal is a continuous-wave signal and the means for launching includes means for imparting a change in a parameter of the continuous-wave signal.

76. Apparatus for assessing the condition of a bony member of a patient comprising:

a. means for launching into the patient, at a first position proximate a bony member, an ultrasound pulse containing energy components in a spectrum from about 100 kHz of about 3.0 MHz;

b. a data acquisition system;

c. at a second position proximate the bony member, substantially opposing said first surface, means for monitoring said ultrasound spectrum, and for generating and supplying to the data acquisition system, for recording thereby, electrical signals corresponding to the energy in the monitored spectrum;

d. means for comparing with a catalog of waveform characteristics from a representative sample of the general public, including for each age range a spectrum of bone conditions, at least one selected waveform characteristic of said electrical signals and for selecting from said catalog that set of waveform characteristics which most closely matches the at least one selected waveform characteristic of the electrical signals; and e. means for determining the condition of the patient's bone by comparing the age and bone condition represented by the matched catalog set of waveform characteristics with the patient's age.

77. Apparatus for evaluating the bone condition of a patient, comprising:

a. means for launching into the patient at a first position proximate a bony member an ultrasound signal having energy components from about 100 kHz to about 3 MHz, such bony member possibly being surrounded by minimal soft tissue;

b. means for monitoring acoustic excitation at a second position proximate said bony member, and for generating electrical signals corresponding to said excitation;

c. the data acquisition system being adapted to record said electrical signals;

d. measuring means for measuring the distance between the first and second position;

e. velocity-determining means responsive to the electrical signals and to the measuring means, for determining the velocity of the ultrasound energy components travelling through the bony member; and f. means responsive to the velocity-determining means, for determining the patient's bone condition from the velocity through the bony member.

78. The apparatus of claim 77 wherein the ultrasound signal comprises at least one pulse.

79. The apparatus of claim 78 wherein the means for launching is adapted to launch a plurality of pulses into the bony member and wherein the velocity-determining means is adapted to determine the average velocities of the respective pulse components for such plurality of pulses.

80. The apparatus of claim 79 wherein the means for determining the patient's bone condition further comprises:

(1) means for providing a template signal;

(2) means for generating a cross-correlation function between the template signal and the averaged signals corresponding to the monitored excitation; and (3) means for evaluating said cross-correlation function to determine the time at which the averaged plurality of pulses first contributed to the monitored excitation.

81. The apparatus of claim 79 wherein the velocity-determining means includes means for compensating for the effect of the soft tissue by adjusting the average pulse transit time through the bone and soft tissue by a soft tissue normalization factor.

82. The apparatus of claim 81 wherein the means for determining the patient's bone condition is adapted to compare the patient's computed average velocity through the bone member to data representing average velocity through the bone measurements for persons of the same age as the patient, including a wide spectrum of bone conditions.

83. The apparatus of claim 81 wherein the means for determining the patient's bone condition is adapted to:

(1) record, for different tests of the same patient over a period of time, the computed average velocity though the bony member;

(2) compare computed average velocities from later tests with computed average velocities from earlier tests; and (3) correlate a positive change in average velocity with respect to time with an improvement in bone condition, and a negative change in average velocity with respect to time with a deterioration in bone condition.

84. Apparatus for evaluating the bone condition of a patient, comprising:

a. means for launching an acoustic signal having energy components in the range between about 100 kHz and about 3.0 MHz, said means having a launching face;

b. means for monitoring excitation in said frequency range, said means having a receiving face;

c. positioning means for locating said first and second transducer means on opposite sides of a bony member of the patient, said bony member being surrounded by soft tissue;

d. signal generator means for triggering the launching transducer means to launch an acoustic signal from the launching face thereof;

e. a data acquisition system electronically connected to said signal generator means and to said monitoring means, said data acquisition system being adapted (1) to determine and record the time at which an acoustic signal is launched;

(2) to monitor and record with respect to time acoustic excitation signals from the monitoring means; and (3) to record the history of the averaged monitored excitation with respect to time;

f. electronic data computation means for processing the recorded data, such computation means (1) comparing an electronic template signal with said recorded averaged time-varying history of said monitored excitation;

(2) maximizing a cross-correlation function between said signal corresponding to said averaged monitored excitation and said template signal, to minimize the effect of noise in obscuring the record of the time of arrival of the acoustic signal at said monitoring means;

(3) determining the time of arrival of said averaged signal response at said monitoring means, and from said time, the duration of travel of said averaged signal through the bone and soft tissue;

g. means for measuring the distance through which an acoustic signal travels between the launching face and the receiving face and for providing to the computation means a signal representing such measurement; and h. the computation means further (4) computing the average velocity of the signals through the bony member and surrounding soft tissue by dividing the measured distance by the computed arrival time;

(5) adjusting the velocity with respect to the patient's soft tissue characteristics, by applying an appropriate soft tissue adjustment factor;

(6) comparing the adjusted velocity to a statistical representation of adjusted velocities for different groups of the population, grouped according to their age and osteoporotic health; and (7) responsive to such comparison, generating a probabilitistic evaluation of the bone condition of the patient.

85. The apparatus of claim 84 wherein the acoustic signal comprises at least one pulse.

86. Apparatus for evaluating the bone condition of a patient, comprising:
   a. means for launching into a first position on the surface of a selected bone of the patient, an acoustic signal containing energy components in the frequency range between about 1.5 and about 3.0 MHz;
   b. means for monitoring excitation transmitted through the patient's bone to a second position on the surface thereof, responsive to said pulse;
   c. a data acquisition system electronically connected to said means for launching and to said means for means for monitoring, said data acquisition system being adapted
      (1) to determine and record the time at which a such signal pulse is launched; and
      (2) to record with respect to time acoustic excitation signals from the monitoring means;
   d. electronic data computation means for processing the recorded data, such computation means
      (1) comparing an electronic template signal with said recorded time-varying history of said monitored excitation;
      (2) maximizing a cross-correlation function between said signal corresponding to said monitored excitation and said template signal, to minimize the effect of noise in obscuring the record of the time of arrival of the pulse at the monitoring means; and
      (3) determining the time of arrival of said signal response at said monitoring means, and from said time, the duration of travel of said signal through the bone and soft tissue;
   e. means for measuring the distance through which an acoustic signal travels between the launching means and the monitoring means and for providing to the computation means a signal representing such measurement; and
   f. the computation means further
      (4) computing the velocity of the acoustic signal through the bony member and surrounding soft tissue, responsive to said distance measurement signal, by dividing the measured distance by the duration of travel of the acoustic signal;
      (5) adjusting the velocity with respect to the patient's soft tissue characteristics, by applying an appropriate soft tissue normalization factor;
      (6) comparing the normalized velocity to a statistical representation of normalized velocities for different groups of the population, grouped according to their age and bone condition; and
      (7) responsive to such comparison, generating a probabilistic evaluation of the bone condition of the patient.

87. The apparatus of claim 86 wherein (i) the acoustic signal includes at least one pulse, (ii) the means for launching is adapted to launch a plurality of pulses into the patient's selected bone, (iii) the data acquisition system is further adapted to average the history of the monitored excitation with respect to time and to record such averaged excitation, and (iv) the recorded time-varying history of the monitored excitation is the averaged time-varying history thereof.

88. A method of measuring, in-vivo, physical properties of a bone surrounded by soft tissue comprising:
   (1) transmitting from a transmitting site, into said soft tissue and bone, a first ultrasonic signal and a second ultrasonic signal;
   (2) receiving at a receiving site, first and second received signals produced, respectively, by the propagation of the first and second ultrasonic signals through the bone and surrounding soft tissue.
   (3) producing from said first received signal information characterizing the soft tissue surrounding the bone; and
   (4) producing from a combination of said first and second received signals a signal characterizing the bone.

* * * * *

UNITED STATES PATENT AND TRADEMARK OFFICE
CERTIFICATE OF CORRECTION

PATENT NO. : 4,913,157
DATED : April 3, 1990
INVENTOR(S) : Pratt, Jr. et al

It is certified that error appears in the above—identified patent and that said Letters Patent is hereby corrected as shown below:

Title page:

The assignee should read:

"Massachusetts Institute of Technology, Cambridge, Mass."

Signed and Sealed this

Third Day of September, 1991

Attest:

HARRY F. MANBECK, JR.

*Attesting Officer*   *Commissioner of Patents and Trademarks*